United States Patent
Li (10) Patent No.: US 9,474,526 B2
(45) Date of Patent: Oct. 25, 2016

(54) TISSUE ANCHOR WITH INSERTION DEVICE

(75) Inventor: Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 945 days.

(21) Appl. No.: 13/605,417

(22) Filed: Sep. 6, 2012

(65) Prior Publication Data

US 2013/0066144 A1 Mar. 14, 2013

Related U.S. Application Data

(60) Provisional application No. 61/532,803, filed on Sep. 9, 2011.

(51) Int. Cl.
| | | |
|---|---|---|
| A61B 17/10 | (2006.01) | |
| A61B 17/064 | (2006.01) | |
| A61B 17/068 | (2006.01) | |
| A61B 17/00 | (2006.01) | |
| A61B 17/29 | (2006.01) | |

(52) U.S. Cl.
CPC ....... A61B 17/0644 (2013.01); A61B 17/0682 (2013.01); A61B 2017/00867 (2013.01); A61B 2017/2902 (2013.01)

(58) Field of Classification Search
CPC .......... A61B 17/0644; A61B 17/0682; A61B 2017/00867; A61B 2017/2902
USPC ........................ 606/92, 142, 151, 157, 219
See application file for complete search history.

(56) References Cited

U.S. PATENT DOCUMENTS

| | | | | |
|---|---|---|---|---|
| 5,304,204 A | * | 4/1994 | Bregen | ............. A61B 17/0644 411/457 |
| 6,086,594 A | | 7/2000 | Brown | |
| 6,193,733 B1 | * | 2/2001 | Adams | ................ A61B 17/122 606/151 |
| 7,169,157 B2 | | 1/2007 | Kayan | |
| 7,556,647 B2 | | 7/2009 | Drews et al. | |
| 7,666,193 B2 | | 2/2010 | Starksen et al. | |

(Continued)

FOREIGN PATENT DOCUMENTS

WO 2013036781 A1 3/2013

OTHER PUBLICATIONS

"Endofast Reliant System for Anterior/Posterior Prolapse Correction", Instructions for Use, IBI Israel Biomedical Innovations Ltd, Jan. 2010, 2 pages.

(Continued)

*Primary Examiner* — Vy Bui
(74) *Attorney, Agent, or Firm* — Brake Hughes Bellermann LLP (57) ABSTRACT

In one embodiment, a medical device includes an elongate member and a tissue anchor. The elongate member defines a lumen. The elongate member has a retention member disposed within the lumen. The tissue anchor has a first arm portion, a second arm portion, and a base portion extending between the first arm portion and the second arm portion. The tissue anchor has a first configuration and a second configuration. The first arm portion is substantially linear when the tissue anchor is in its first configuration and the first arm portion is non-linear when the tissue anchor is in its second configuration. The tissue anchor is biased to its second configuration. The tissue anchor is configured to be disposed within the lumen defined by the elongate member such that the retention member engages the tissue anchor to help retain the tissue anchor in its first configuration.

17 Claims, 9 Drawing Sheets

(56) References Cited

U.S. PATENT DOCUMENTS

| | | |
|---|---|---|
| 7,681,772 B2 | 3/2010 | Green et al. |
| 2005/0288689 A1* | 12/2005 | Kammerer ......... A61B 17/0469 606/142 |
| 2007/0088390 A1 | 4/2007 | Paz et al. |
| 2010/0044410 A1 | 2/2010 | Argentine et al. |
| 2010/0191262 A1 | 7/2010 | Harris et al. |

OTHER PUBLICATIONS

International Search Report and Written Opinion received for PCT Patent Application No. PCT/US12/054187, mailed on Oct. 18, 2012, 13 pages.

International Preliminary Report received for PCT Patent Application No. PCT/US12/054187, mailed on Mar. 20, 2014, 9 pages.

* cited by examiner

TISSUE ANCHOR WITH INSERTION DEVICE

CROSS-REFERENCE TO RELATED APPLICATION

This application is a Nonprovisional of, and claims priority to, U.S. Patent Application No. 61/532,803, filed Sep. 9, 2011, entitled "TISSUE ANCHOR WITH INSERTION DEVICE", which is incorporated by reference herein in its entirety.

TECHNICAL FIELD

This disclosure relates generally to medical devices and more particularly to medical devices that include fixation devices or tissue anchors.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures include placing a support member or implant into the body of the patient such that the support member or implant provides support to a portion of the body of the patient. Specifically, in some medical procedures, the support member or implant may be fixed or coupled to the body of the patient at various locations within the body of the patient and a support portion of the support member or implant may be placed beneath the portion of the body to be supported.

In some known medical procedures, tissue anchors or fixation devices are used fix or couple portions of the support member to portions of the body of the patient. A need exists for fixation devices or tissue anchors that effectively retain a support member in place within a body of a patient. A need also exists for a tool for effectively placing such fixation or tissue anchors inside the body of the patient.

SUMMARY

In one embodiment, a medical device includes an elongate member and a tissue anchor. The elongate member defines a lumen. The elongate member has a retention member disposed within the lumen. The tissue anchor has a first arm portion, a second arm portion, and a base portion extending between the first arm portion and the second arm portion. The tissue anchor has a first configuration and a second configuration. The first arm portion is substantially linear when the tissue anchor is in its first configuration and the first arm portion is non-linear when the tissue anchor is in its second configuration. The tissue anchor is biased to its second configuration. The tissue anchor is configured to be disposed within the lumen defined by the elongate member such that the retention member engages the tissue anchor to help retain the tissue anchor in its first configuration.

In another embodiment, an apparatus includes an elongate member, a retention member, and a pusher. The elongate member has a first end portion and a second end portion. The elongate member defines a lumen configured to receive a tissue anchor such that a tissue piercing portion of the tissue anchor is disposed within the lumen. The retention member is disposed within the lumen defined by the elongate member. The retention member is configured to help retain at least a portion of the tissue anchor in a linear configuration. The pusher is configured to move within the lumen from a first position within the lumen to a second position within the lumen. The pusher is configured contact and force the tissue anchor from a location within the lumen to a location outside of the lumen in response to the pusher being moved from the first position to the second position.

In yet another embodiment, a method of placing an anchor within a body of a patient includes (1) inserting a medical device within the body of the patient, the medical device includes an elongate member defining a lumen, and a tissue anchor disposed within the lumen, the tissue anchor has a first configuration in which an arm portion of the of the tissue anchor is substantially linear and a second configuration in which the arm portion is non-linear, (2) retaining the tissue anchor in its first configuration while the tissue anchor is disposed within the lumen defined by the elongate member, and (3) moving the tissue anchor from a location within the lumen defined by the medical device to a location outside of the lumen.

DETAILED DESCRIPTION

The devices and methods described herein are generally directed to procedures for placing implants within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved.

Various fixation devices or tissue anchors, delivery devices, and methods are described for delivering and securing an implant within the body of the patient. The implants, fixation devices, delivery devices, and procedures described herein may be used in a female patient or a male patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

Figure 1:
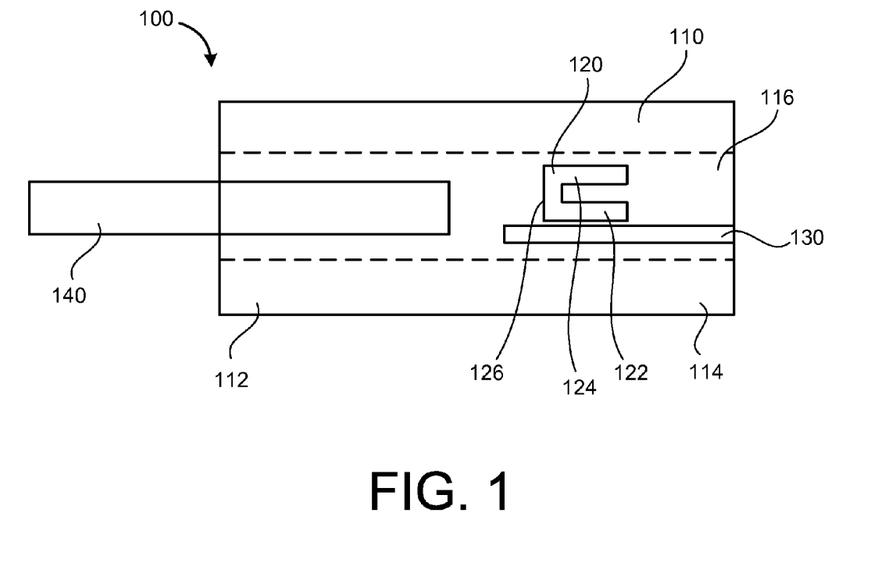
FIG. 1 is a schematic illustration of an apparatus according to an embodiment of the invention.

FIG. 1 is a schematic illustration of an apparatus or medical device 100 according to an embodiment of the invention. The apparatus or medical device 100 includes an elongate member 110, a tissue anchor (or fixation device) 120, and a retention member 130. The illustrated embodiment also includes a pusher 140.

The apparatus 100 is configured to be inserted into a body of a patient such that at least a portion of the apparatus 100 is disposed within the body of the patient. As will be discussed in more detail below, the apparatus is configured to be placed adjacent a desired coupling or fixation location within the body.

The elongate member 110 includes a first end portion 112 and a second end portion 114. The elongate member 110 defines a lumen 116 (shown in dashed lines in FIG. 1). In some embodiments, the lumen 116 extends from the first end portion 112 to the second end portion 114. In some embodiments, the elongate member 110 defines an opening at the first end portion 112 and an opening at the second end portion 114 and the lumen 116 extends between the opening at the first end portion 112 and the opening at the second end portion 114. In other embodiments, the lumen only extends through a portion of the length of the elongate member 110. The lumen 116 is configured to receive and house various components of the apparatus 100 as will be described in detail below.

The tissue anchor or fixation device 120 is configured to be placed within a body of a patient and to be fixedly coupled to a portion of the body of the patient. For example, in some embodiments, the tissue anchor 120 is configured to engage a bodily implant and be coupled to body tissue within the body of the patient to fixedly couple the implant to the body tissue.

In some embodiments, the tissue anchor or fixation device 120 includes a first arm portion 122, a second arm portion 124, and a base portion 126 disposed between the first arm portion 122 and the second arm portion 124. The tissue anchor 120 is configured to be disposed in a first configuration and a second configuration. For example, in some embodiments the tissue anchor 120 is in an extended configuration or position when the tissue anchor 120 is in its first configuration and is in a collapsed configuration or position when the tissue anchor 120 is in its second configuration. In some embodiments, the first arm 122 and the second arm 124 of the tissue anchor 120 are disposed in a linear or substantially linear configuration when the tissue anchor 120 is disposed in its first configuration. The first arm 122 and the second arm 124 of the tissue anchor are disposed in a curved configuration when the tissue anchor 120 is in its second configuration.

In some embodiments, the tissue anchor 120 is configured to be disposed within the lumen 116 defined by the elongate member 110 while the tissue anchor 120 is in its first configuration. In some embodiments, the entire tissue anchor 120 is configured to be disposed within the lumen 116. In some embodiments, the tissue anchor 120 includes a tissue piercing portion. The tissue piercing portion is configured to pierce or be inserted into bodily tissue. In such embodiments, the tissue piercing portion is configured to be disposed within the lumen 116 defined by the elongate member 110 while the tissue anchor 120 is in its first configuration.

In the illustrated embodiment, the apparatus 100 includes a retention member 130. The retention member 130 is disposed within the lumen 116 defined by the elongate member 120. The retention member 130 is configured to engage the tissue anchor 120 while the tissue anchor 120 is disposed in the lumen 116 to help retain the tissue anchor 120 in its first configuration.

In some embodiments, the retention member 130 is formed of a resilient material and includes a first portion and a second portion. The first portion is configured to engage the first arm portion 122 of the tissue anchor 120 to help retain the first arm portion 122 of the tissue anchor 120 in a substantially linear configuration or position. The second portion of the retention member 130 is configured to engage the second arm portion 124 of the tissue anchor 120 to help retain the second arm portion 124 of the tissue anchor 120 is a substantially linear configuration or position.

In some embodiments, the retention member 130 includes a flexible portion that is configured to flex from a first orientation or configuration to a second orientation or configuration. For example, in some embodiments, the flexible portion is configured to move from its first orientation to its second orientation to allow the tissue anchor 120 to pass by and be moved away from the retention member. In some embodiments, the flexible portion is biased to its first orientation or configuration.

In the illustrated embodiment, the apparatus 100 includes a pusher 140. The pusher 140 is configured to be disposed within the lumen 116 defined by the elongate member 110. For example, in some embodiments, the pusher 140 is configured to be disposed within the lumen 116 such that a portion of the pusher 140 is disposed within the lumen 116 and a portion of the pusher 140 is disposed outside of the lumen 116.

The pusher 140 is configured to move from a first location to a second location with respect to the elongate member 110. For example, in some embodiments, the pusher 140 is configured to move from a first location within the lumen 116 to a second location within the lumen 116 different than the first location. The pusher 140 is configured to contact the tissue anchor 120 while the tissue anchor 120 is disposed within the lumen 116 and force the tissue anchor 120 out of the lumen 116 defined by the elongate member 110. For example, in some embodiments, when the pusher 140 is at its first position within the lumen 116 the pusher 140 does not contact the tissue anchor 120. As the pusher 140 is moved from its first position to its second position, the pusher 140 contacts the tissue anchor 120 and moves the tissue anchor 120 within the lumen 116. In some embodiments, the pusher 140 is configured to expel or push the tissue anchor 120 to a location outside of the lumen 116 when the pusher 140 is in its second position.

In some embodiments, the lumen 116 defined by the elongate member 110 is configured to house or receive a plurality of tissue anchors. For example, in some embodiments, the lumen 116 of the elongate member 110 is configured to house or receive two tissue anchors. In some embodiments, the tissue anchors may be disposed serially or end to end within the lumen 116. In such embodiments, the pusher 140 may be configured to contact and move one of the tissue anchors, which may in turn be configured to contact and move the other of the tissue anchors.

In use, a tissue anchor 120 may be disposed within the lumen 116 defined by the elongate member 100 such that the tissue anchor 120 is retained in its first or expanded configuration (i.e., such that the first arm portion 122 and the second arm portion 124 of the tissue anchor 120 are disposed in a linear configuration). The apparatus 100 may then be inserted into a body of a patient. For example, in some implementations, the apparatus 100 may be inserted into a body of a patient through a vaginal incision. An end portion, such as the second end portion 114 (a distal end portion) of the elongate member 110 may be disposed adjacent to the bodily tissue into which the tissue anchor 120 is to be inserted. In some embodiments, a bodily implant, such as a mesh type bodily implant, may be disposed between the second end portion 114 of the elongate member 110 and the tissue.

The pusher 140 may then be moved with respect to the elongate member 110 within the lumen 116 defined by the elongate member 110. For example, the pusher may be moved from a first position to a second position. As the pusher is moved from its first position or location within the lumen 116 to its second position or location within the lumen 116, the pusher 140 contacts and moves the tissue anchor 120 from a location within the lumen 116 to a location outside of the lumen.

In some embodiments, as the tissue anchor 120 is moved to a location or position outside of the lumen 116, the tissue anchor 120 will pierce the bodily implant and the desired tissue. Additionally, once the tissue anchor 120 is disposed outside of the lumen (and away from the retainer 130), the tissue anchor 120 will assume its second configuration. In other words, the first arm portion 122 and the second arm portion 124 will assume their curved configurations. Accordingly, the tissue anchor 120 will be embedded within the bodily tissue and the first arm portion 122 and the second arm portion 124 will grasp or secure a portion of the bodily tissue to fixedly couple the tissue anchor 120 (and the bodily implant) to the bodily tissue.

In some embodiments, the medical device includes a second tissue anchor. In such embodiments, the medical device may then be moved to another location within the body (and disposed adjacent different or another portion of bodily tissue). The second tissue anchor may then be inserted to such portion of bodily tissue.

Figure 2:
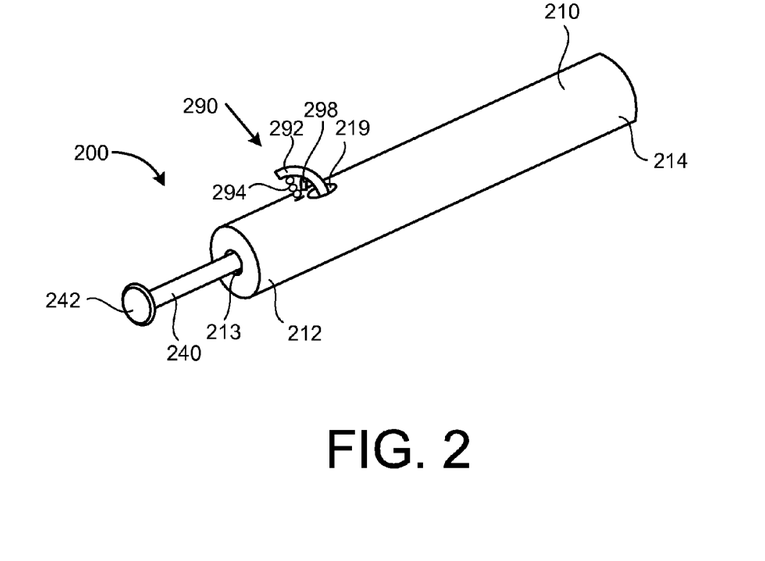
FIG. 2 is a perspective view of an apparatus according to an embodiment of the invention.
Figure 3A:
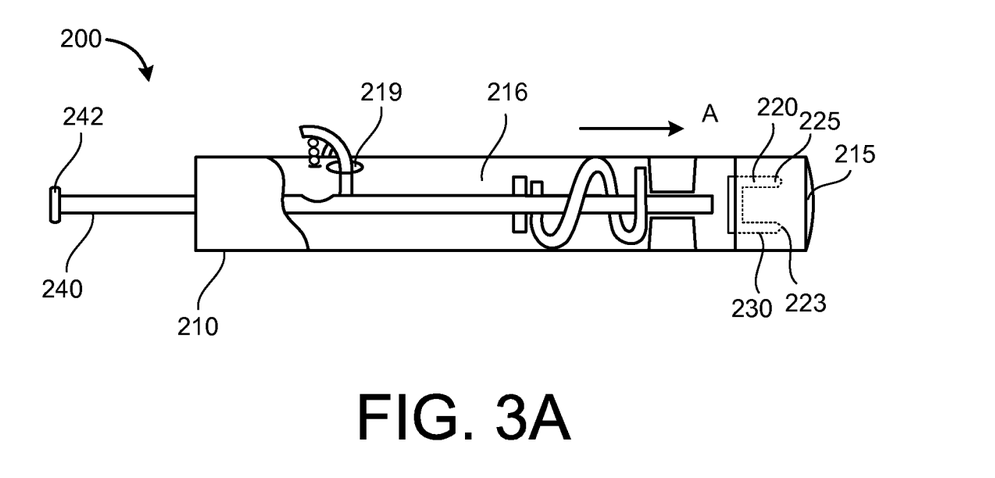
FIGS. 3A and 3B are break away side views of the apparatus of FIG. 2.
Figure 3B:
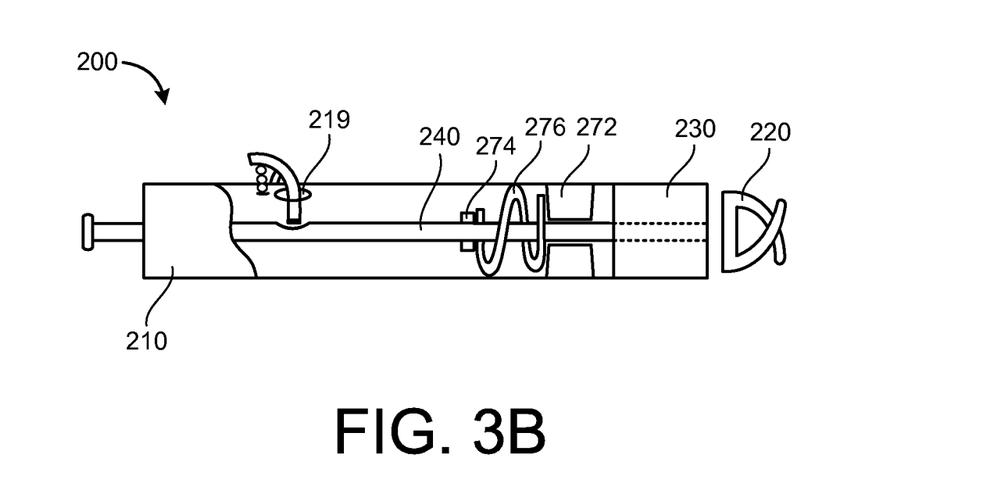

FIG. 2 is a perspective view of an apparatus or medical device 200 according to an embodiment of the invention. FIG. 3A is a break away side view of the apparatus 200 in a first configuration. FIG. 3B is a break away side view of the apparatus 200 in a second configuration. The apparatus 200 includes an elongate member 210, a tissue anchor (or fixation device) 220, and a retention member 230. The illustrated embodiment also includes a pusher 440.

The apparatus 200 is configured to be inserted into a body of a patient such that at least a portion of the apparatus 200 is disposed within the body of the patient. In some embodiments, the apparatus 200 is configured to be inserted into a body of a patient such that a distal end portion 214 of the elongate member 210 is disposed adjacent a desired coupling or fixation location within the body.

The elongate member 210 includes a first or proximal end portion 212 and the second or distal end portion 214. The elongate member 210 defines a lumen 216. In the illustrated embodiment, the lumen 216 extends from the first end portion 212 to the second end portion 214. In the illustrated embodiment, the elongate member 210 defines an opening 213 at the first end portion 212 and an opening 215 at the second end portion 214 and the lumen 216 extends between the opening 213 at the first end portion 212 and the opening 215 at the second end portion 214. In other embodiments, the lumen only extends through a portion of the length of the elongate member.

The lumen 216 is configured to receive and house various components of the apparatus 200 as will be described in detail below.

Figure 7:
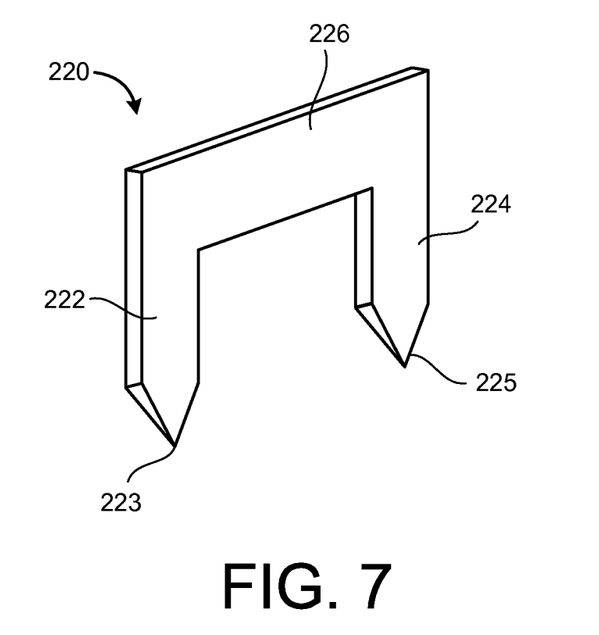
FIG. 7 is a perspective view of a tissue anchor of the apparatus of FIG. 2 in a first configuration.
Figure 8:
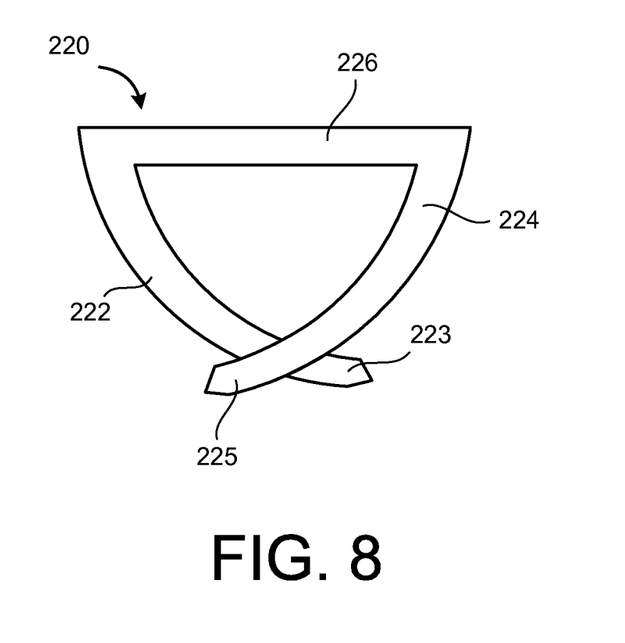
FIG. 8 is a side view of the tissue anchor of FIG. 7 in a second configuration.

FIG. 7 is a perspective view of the tissue anchor or fixation device 220 in a first configuration. FIG. 8 is a side view of the tissue anchor 220 in a second configuration. The tissue anchor or fixation device 220 is configured to be placed within a body of a patient and to be fixedly coupled to a portion of the body of the patient. For example, in some embodiments, the tissue anchor 220 is configured to engage a bodily implant and be coupled to body tissue within the body of the patient to fixedly couple the implant to the body tissue. In other embodiments, the tissue anchor or fixation device 220 is configured to couple a first bodily tissue potion to a second bodily tissue portion.

The tissue anchor or fixation device 220 includes a first arm portion 222, a second arm portion 224, and a base portion 226 disposed between the first arm portion 222 and the second arm portion 224. The tissue anchor 220 is configured to be disposed in a first configuration (as illustrated in FIG. 7) and a second configuration (as illustrated in FIG. 8). The tissue anchor 220 is in an extended configuration or position when the tissue anchor 220 is in its first configuration and is in a collapsed configuration or position when the tissue anchor 220 is in its second configuration. In the illustrated embodiment, the first arm 222 and the second arm 224 of the tissue anchor 220 are disposed in a linear or substantially linear configuration when the tissue anchor 220 is disposed in its first configuration. The first arm 222 and the second arm 224 of the tissue anchor are disposed in a curved configuration when the tissue anchor 220 is in its second configuration. In the illustrated embodiment, the first arm portion 222 and the second arm portion 224 cross when the tissue anchor 220 is in its second configuration.

In some embodiments, the tissue anchor 220 is biased to its second configuration (as illustrated in FIG. 8). In other words, in some embodiments, the tissue anchor 220 is biased to a configuration in which the first arm portion 222 and the second arm portion 224 are in a curved configuration. In some embodiments, the tissue anchor 220 is formed of a shape member material. For example, in some embodiments, the tissue anchor 220 is formed of nitinol or a shape memory polymer.

In the illustrated embodiment, the tissue anchor includes a first tissue piercing portion 223 and a second tissue piercing portion 225. The first tissue piercing portion 223 is disposed at an end portion of the first arm portion 222 (opposite the base portion 226). The second tissue piercing portion 225 is disposed at an end portion of the second arm portion 224 (opposite the base portion 226). The first and second tissue piercing portions 223 and 225 are configured to pierce bodily tissue when the tissue anchor 220 is placed against or into bodily tissue. In some embodiments, the tissue piercing portions 223 and 225 include sharp portions configured to pierce bodily tissue.

The tissue anchor 220 is configured to be disposed within the lumen 216 defined by the elongate member 210 while the tissue anchor 220 is in its first configuration. In some embodiments, the entire tissue anchor 220 is configured to be disposed within the lumen 216. In the illustrated embodiment, the tissue piercing portions 223 and 225 are configured to be disposed within the lumen 216. For example, the tissue piercing portions 223 and 225 are configured to be disposed within the lumen 216 while the apparatus 200 is inserted into the body of the patient.

In the illustrated embodiment, the tissue anchor 220 is integrally or monolithically formed. In other words, the first arm portion 222, the second arm portion 224, and the base portion 226 are formed of a single piece of material. In other embodiments, the portions of the tissue anchor are formed of separate pieces of material. In some such embodiments, the first arm portion and the second arm portion may be movably coupled to the base portion 226. The tissue anchor may include a bias member configured to bias the movably arm members into their expanded configurations.

Figure 4:
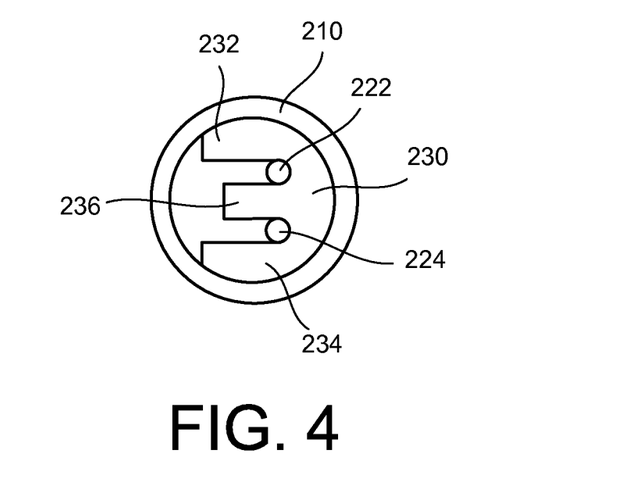
FIG. 4 is an end view of the apparatus of FIG. 2.
Figure 5:
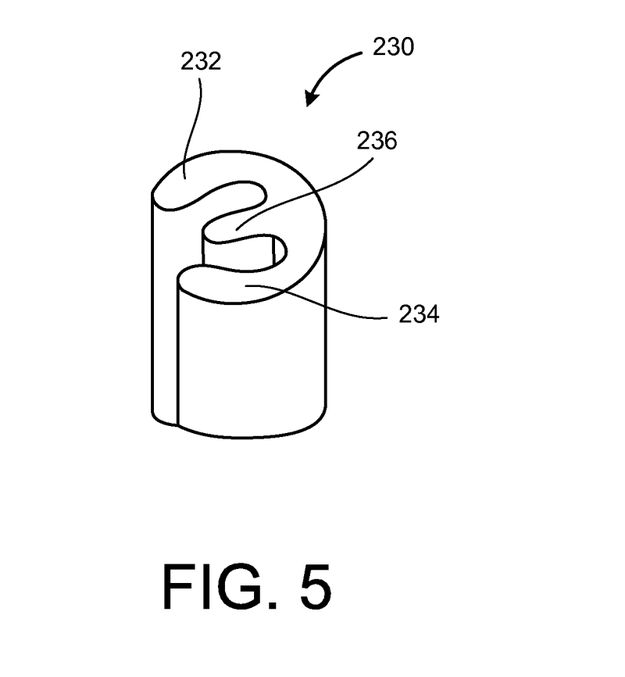
FIG. 5 is a perspective view of a retention member of the apparatus of FIG. 2.

FIG. 4 is an end view of the apparatus 200. FIG. 5 is a perspective view of the retention member 230. The retention member 230 is disposed within the lumen 216 defined by the elongate member 210. The retention member 230 is configured to engage the tissue anchor 220 while the tissue anchor 220 is disposed in the lumen 216 to help retain the tissue anchor 220 in its first configuration.

In the illustrated embodiment, the retention member 230 is formed of a resilient material such as a resilient, shape member polymer. The retention member includes a first portion 232 and a second portion 234. The first portion 232 is configured to engage the first arm portion 222 of the tissue anchor 220 to help retain the first arm portion 222 of the tissue anchor 220 in a substantially linear configuration or position. Specifically, in the illustrated embodiment, the first portion 232 of the retention member 230 is configured to engage the fist arm portion 222 of the tissue anchor 220 when the tissue anchor 220 is disposed within the lumen 216 of the elongate member 210. The second portion 234 of the retention member 230 is configured to engage the second arm portion 224 of the tissue anchor 220 to help retain the second arm portion 224 of the tissue anchor 220 is a substantially linear configuration or position when the tissue anchor 220 is disposed within the lumen 216.

In the illustrated embodiment, the retention member 130 includes a flexible portion 236 that is configured to flex from a first orientation or configuration to a second orientation or configuration. For example, in some embodiments, the flexible portion is configured to move from its first orientation in the direction of arrow A to its second orientation to allow the tissue anchor 220 to pass by and be moved away from the retention member. In some embodiments, the flexible portion 236 is biased to its first orientation or configuration.

The apparatus 200 includes a pusher 240. The pusher 240 is configured to be disposed within the lumen 216 defined by the elongate member 210. For example, the pusher 240 is configured to be disposed within the lumen 216 such that a portion of the pusher 240 is disposed within the lumen 216 and a portion of the pusher 240 is disposed outside of the lumen 216. In the illustrated embodiment, the pusher includes an actuator 242.

The pusher 240 is configured to move from a first location to a second location with respect to the elongate member 210. For example, in the illustrated embodiment, the pusher 240 is configured to move from a first location within the lumen 216 to a second location within the lumen 216 different than the first location. The pusher 140 is configured to contact the tissue anchor 220 while the tissue anchor 220 is disposed within the lumen 216 and force the tissue anchor 220 out of the lumen 216 defined by the elongate member 210. When the pusher 240 is at its first position within the lumen 216 the pusher 240 does not contact the tissue anchor 220 (as illustrated in FIG. 3A). As the pusher 240 is moved from its first position to its second position (for example in the direction of arrow A), the pusher 240 contacts the tissue anchor 220 and moves the tissue anchor 220 within the lumen 216. As illustrated in FIG. 3B, in the illustrated embodiment, the pusher 240 is configured to expel or push the tissue anchor 220 to a location outside of the lumen 216 when the pusher 240 is in its second position.

In some embodiments, the pusher 240 is biased to its first position (the position in which it does not contact or place force on the tissue anchor 220). In the illustrated embodiments, the apparatus 200 includes bias mechanism 270. The bias mechanism 270 is configured to force or bias the pusher 240 into its first position within the lumen 216. The bias mechanism 270 includes a first contact portion 272 coupled within the lumen 216, a second contact portion 274 coupled to the pusher 240, and a spring member 276 disposed between the first contact portion 272 and the second contact portion 274. The bias member 276 is configured to engage the first contact portion 272 and the second contact portion 274 and to bias the first contact portion 272 away from the second contact portion 274.

In some embodiments, the first contact portion 272 of the bias mechanism 270 is a single member that extends circumferentially about the internal surface of the lumen 216. In other embodiments, the first contact portion 272 includes one or more portions disposed about the internal surface of the lumen 216. In some embodiments, the first contact portion 272 is integrally or unitarily formed with the elongate member 210.

In some embodiments, the second contact portion 274 of the bias mechanism 270 is a single member that extends circumferentially about the pusher 240. In other embodiments, the second contact portion 274 includes one or more portions disposed on the pusher 240. In some embodiments, the second contact portion 274 is integrally or unitarily formed with the pusher 240.

In the illustrated embodiment, the bias member 276 is a spring member. In other embodiments, the bias member 274 is a different type of member configured to bias the first contact portion 272 away from the second contact portion 274.

In the illustrated embodiment, the pusher 240 includes an actuator 242. The actuator 242 is configured to facilitate the movement of the pusher 240 from its first position to its second position. For example, the actuator 242 is configured to be engaged by a user (such as a figure of a physician) to allow the user to force the pusher 240 from its first position to its second position.

In the illustrated embodiment, the apparatus 200 includes a stop mechanism 290. The stop mechanism 290 is configured to prevent the pusher from moving too far within the lumen 216 defined by the elongate member 210. For example, the stop mechanism 290 is configured to prevent the pusher from moving to a location distally or beyond its second position.

In the illustrated embodiment, the stop mechanism 290 includes a projection 292 that extends from a location outside of the lumen 216 to a location inside of the lumen 216. The projection 292 is pivotally coupled to member 298 which is fixedly coupled to the elongate member 210. The projection 292 extends through an opening 219 defined by the elongate member 210. The projection 292 is configured to move from a first position to a second position and is bias to its first position. In the illustrated embodiment, a bias member 294, such as a spring member, is configured to bias the projection 292 to its first position. When the projection 292 is in its first position, it is configured to engage a receiving portion 249 of the pusher 240. The engagement of the projection 292 with the receiving portion 249 (as illustrated in FIG. 3B) helps prevent the pusher 240 from moving beyond or distally of its second position. In some embodiments, the engagement of the projection 292 with the receiving portion 249 will provide an indication to the user (such as the physician) that the pusher 240 has reached its second position (and the tissue anchor 220 has been expelled or pushed out of the lumen 216).

When the projection 292 is in its second position it does not engage the receiving portion 249 of the pusher 240. Accordingly, the pusher 240 is moved back to its first position. In the illustrated embodiment, a user may depress the projection 292 against the bias member 294 to pivot the projection 292 with respect to member 298 to its second position. The bias mechanism 270 may then move or bias the pusher 240 back to its first position.

Figure 6A:
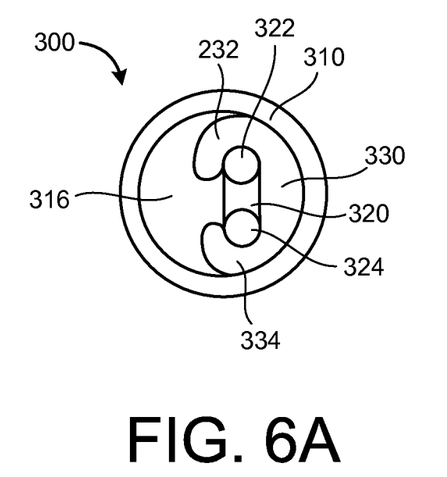
FIG. 6A is an end view of an apparatus according to an embodiment of the invention.
Figure 6B:
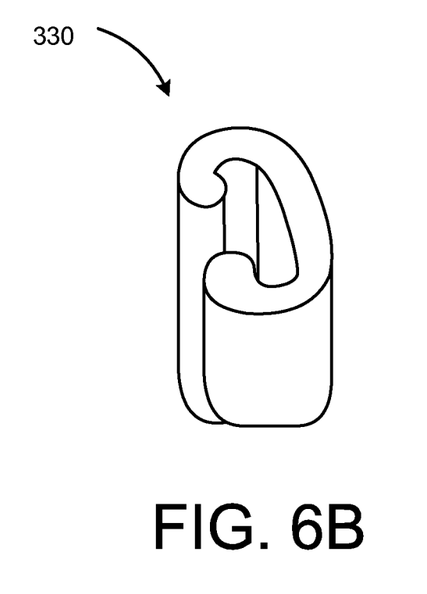
FIG. 6B is a perspective view of a retention member of the apparatus of FIG. 6A.

FIG. 6A is an end view of an apparatus 300 that includes an elongate member 300 and a retention member 330 according to an embodiment of the invention. FIG. 6B is a perspective view of the retention member 330. The retention member 330 is disposed within the lumen 316 defined by the elongate member 310. The retention member 330 is configured to engage the tissue anchor 320 while the tissue anchor 320 is disposed in the lumen 316 to help retain the tissue anchor 320 in its first configuration.

In the illustrated embodiment, the retention member 330 is formed of a resilient material such as a resilient, shape member polymer. The retention member includes a first portion 332 and a second portion 334. The first portion 332 is configured to engage the first arm portion 322 of the tissue anchor 320 to help retain the first arm portion 322 of the tissue anchor 320 in a substantially linear configuration or position. Specifically, in the illustrated embodiment, the first portion 332 of the retention member 330 is configured to engage the fist arm portion 322 of the tissue anchor 320 when the tissue anchor 320 is disposed within the lumen 316 of the elongate member 310. The second portion 334 of the retention member 330 is configured to engage the second arm portion 324 of the tissue anchor 320 to help retain the second arm portion 324 of the tissue anchor 320 is a substantially linear configuration or position when the tissue anchor 320 is disposed within the lumen 316.

The illustrated embodiments, illustrate the retention member being separate from the elongate member. In such embodiments, the retention member is disposed within the lumen of the elongate member and is coupled to the elongate member. For example, the retention member may be coupled within the lumen defined by the elongate member via an adhesive or other coupling mechanism. In other embodiments, the retention member is integrally or monolithically formed with the elongate member.

Figure 9:
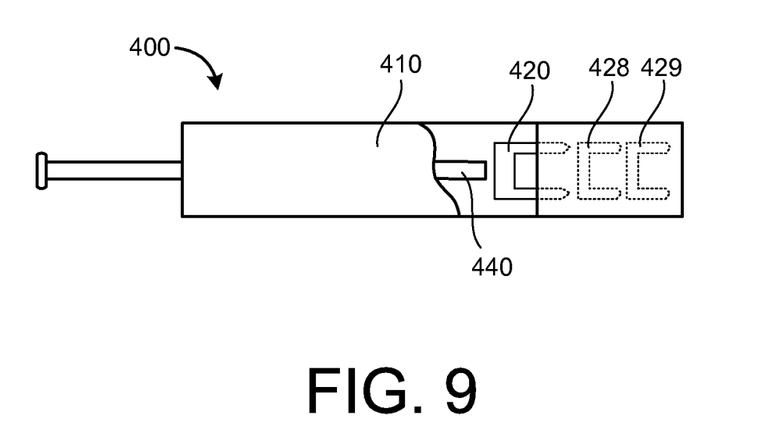
FIG. 9 is break away side view of an apparatus according to an embodiment of the invention.

In some embodiments, the lumen defined by the elongate member is configured to house or receive a plurality of tissue anchors. FIG. 9 is a break away side view of an apparatus 400 according to another embodiment. As illustrated, the elongate member 410 of the apparatus 400 defines a lumen 416. A plurality of tissue anchors 420, 428 and 429 are disposed within the lumen 416 and retained in their expanded configuration. The tissue anchors 420, 428, and 429 are disposed within the lumen 416 in an end to end relationship. Said another way, the distal end portion of tissue anchor 420 is disposed adjacent a proximal end portion of tissue anchor 428. Similarly, a distal end portion of tissue anchor 428 is disposed adjacent a proximal end portion of tissue anchor 429.

In the illustrated embodiment, each of the tissue anchors 420, 428, and 429 may be placed into bodily tissue. Specifically, each tissue anchor 420, 428, and 429 may be placed in different bodily tissue or different portions of bodily tissue. As the pusher 440 is advanced within the lumen 416 defined by the elongate member, the pusher may contact and advance tissue anchor 420, which will contact and advance tissue anchor 428, which will contact and advance tissue anchor 429 to a location outside of the body. The apparatus 400 may then be moved within the body of the patient (adjacent another portion of bodily tissue) and the pusher may be moved to force tissue anchor 428 to a location outside of the lumen 416 and into the bodily tissue.

Figure 10:
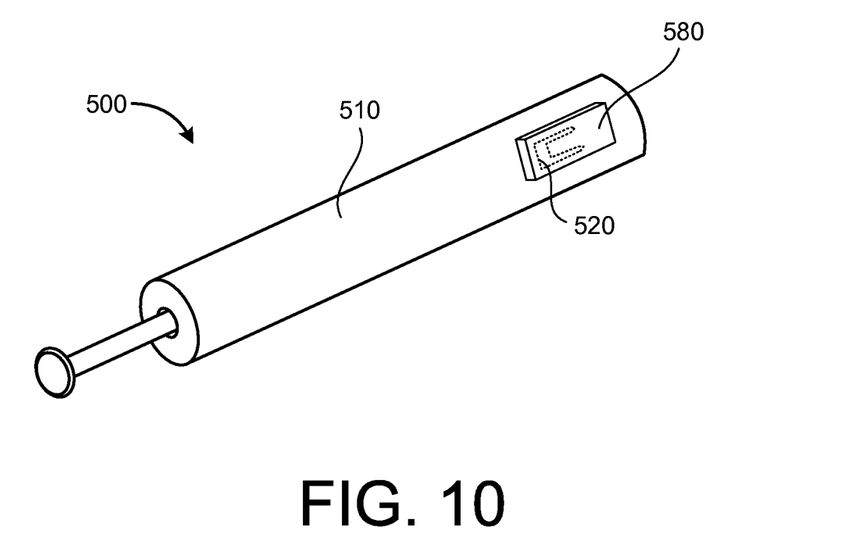
FIG. 10 is a perspective view of an apparatus according to an embodiment of the invention.

FIG. 10 is a perspective view of an apparatus 500 according to another embodiment of the invention. The apparatus 500 includes a cassette 580. The cassette 580 houses a plurality of tissue anchors 520. The cassette 580 is coupled to the elongate member 510 such that the cavity that houses the tissue anchors 520 communicates with the lumen defined by the elongate member 510. For example, in some embodiments, the cavity that houses the tissue anchors 520 communicates with the lumen defined by the elongate member 510 via an opening in the sidewall of the elongate member 510.

The cassette 580 is configured to advance the plurality of tissue anchors that are housed therein into position within the lumen of the elongate member 510 in response a tissue anchor being expelled from the lumen of the elongate member 510. For example, in some embodiments, the cassette 580 may include a bias mechanism configured to advance the tissue anchors into the lumen defined by the elongate member 510.

Figure 11:
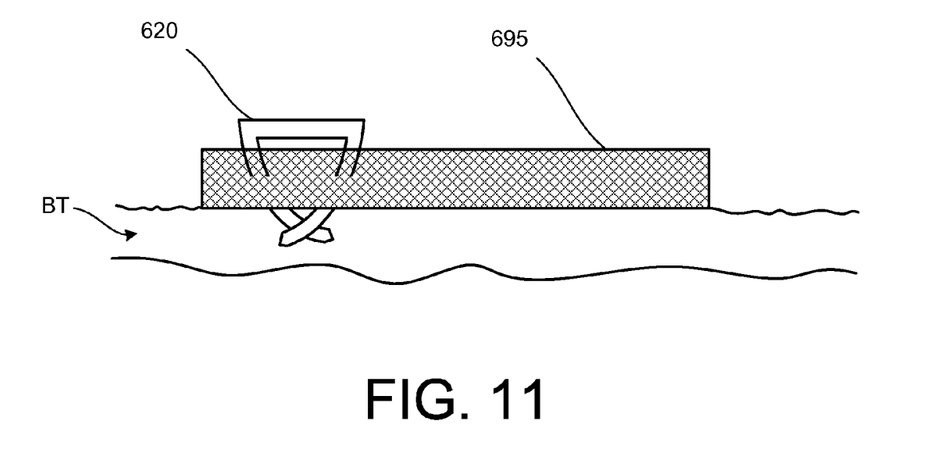
FIG. 11 is a perspective view of a tissue anchor engaged with a bodily implant.

FIG. 11 illustrates a tissue anchor 620 engaged with an implant 695 and bodily tissue BT. As illustrated, the tissue anchor 620 extends through the implant 695 and into bodily tissue. The tissue anchor 620 is disposed in its second configuration. Accordingly, the arm portions of the tissue anchor 620 are curved and are configured to help couple the tissue anchor 620 (and the implant 695) to the bodily tissue BT. In some embodiments, the arm portions of the tissue anchor 620 are configured to grasp bodily tissue to help secure or couple the tissue anchor 620 (and the implant 695) to the bodily tissue BT.

The implant 695 is configured to be placed with a body of a patient. In some embodiments, the implant 695 is configured to be placed within a body of a patient such that it provides support to a portion of the body of the patient. The implant may be formed of any biocompatible material. For example, the implant 695 may be formed of a natural or synthetic material or a combination of such materials. In the illustrated embodiment, the implant 695 includes a mesh portion.

Figure 12:
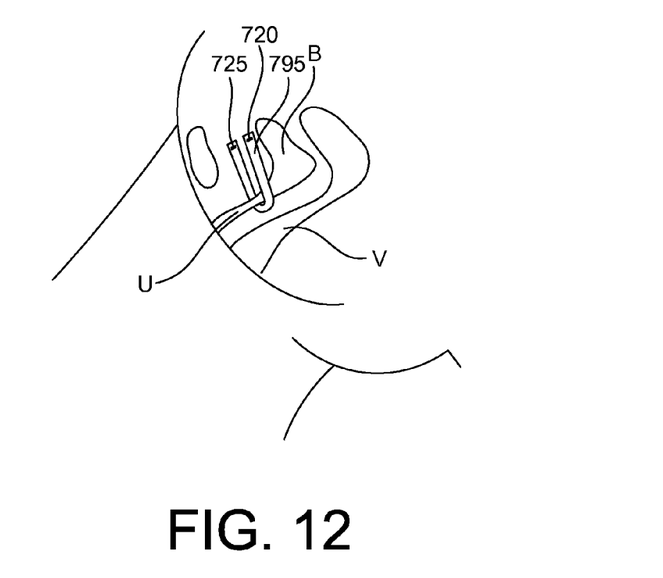
FIGS. 12 and 13 are schematic illustrations of implants disposed within a body of a patient.

FIG. 12 schematically illustrates an implant 795 disposed within a pelvic region of a patient. The end portions of the implant 795 are coupled to bodily tissue via tissue anchors 720 and 725. The implant 795 extends beneath the urethra U of the patient and is configured to provide support to the urethra U. In some embodiments, the implant 795 may be inserted into the body of the patient (using an apparatus as described above) via an incision in the wall of the vagina V.

Figure 13:
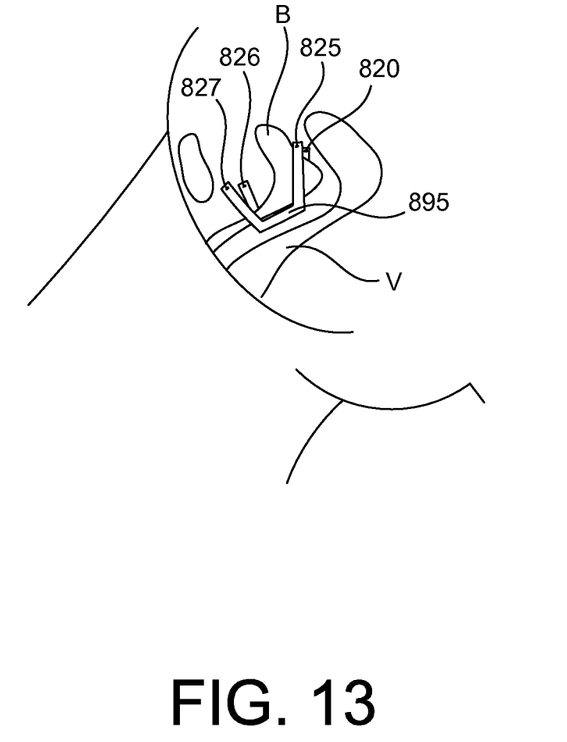

FIG. 13 schematically illustrates an implant 895 disposed within a pelvic region of a patient. The end portions or arms of the implant 895 are coupled to bodily tissue via tissue anchors 820, 825, 826, and 827. The implant 895 is extends beneath the bladder B of the patient and is configured to provide support to the bladder B. In some embodiments, the implant 895 may be inserted into the body of the patient (using an apparatus as described above) via an incision in the wall of the vagina V.

Figure 14:
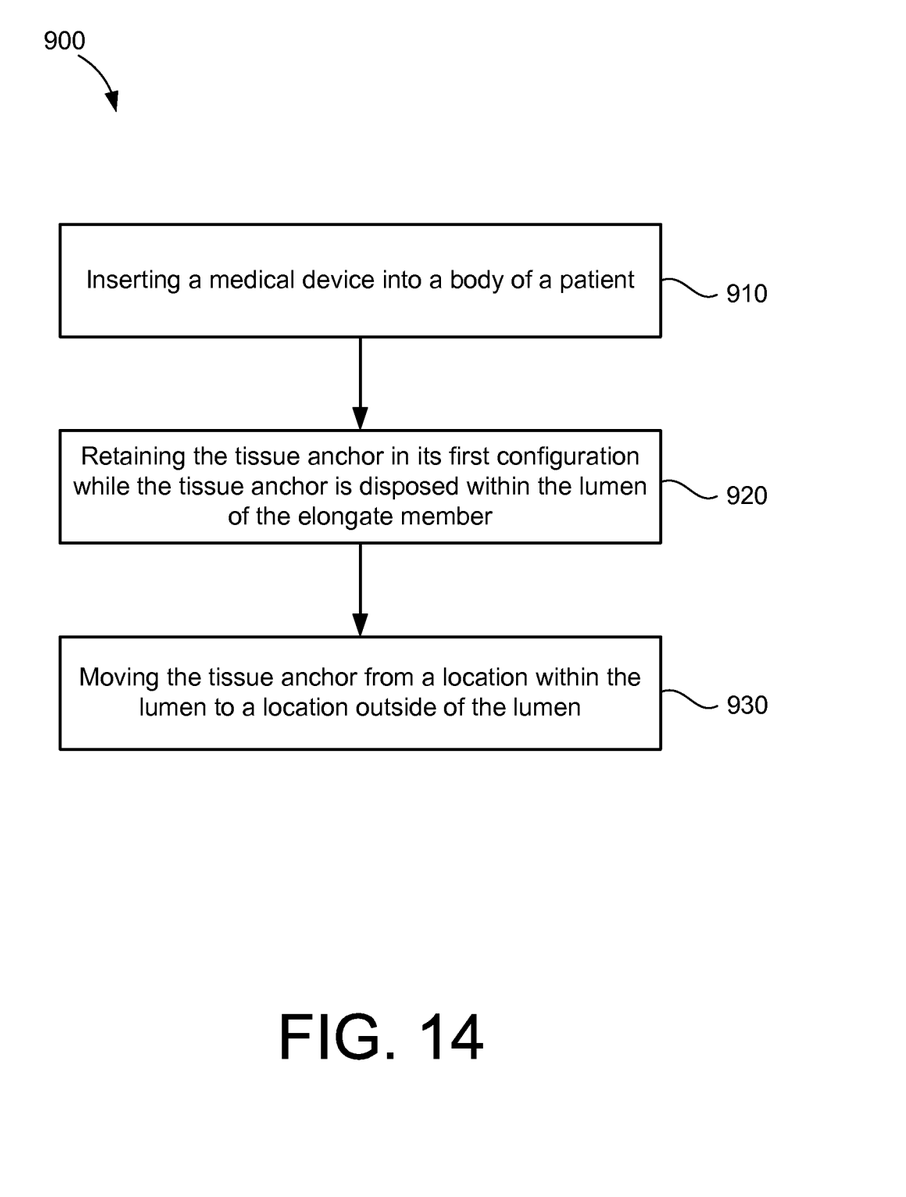
FIG. 14 is a flow chart of a method of placing an implant within a body of a patient according to an embodiment of the invention.

FIG. 14 is a flow chart of a method 900 of placing a tissue anchor within bodily tissue according to an embodiment of the invention. At 910, a medical device is inserted into a body of the patient. In some embodiments, the medical device includes an elongate member defining a lumen and a tissue anchor disposed within the lumen. The tissue anchor has a first configuration in which an arm portion of the tissue anchor is substantially linear and a second configuration in which the arm portion is non-linear. The tissue anchor is biased to its first configuration. At 920, the tissue anchor is retained in its first configuration while the tissue anchor is disposed within the lumen defined by the elongate member. At 930, the tissue anchor is moved from a location within the lumen defined by the medical device to a location outside of the lumen.

In some embodiments, the tissue anchor is disposed within the lumen such that the entire tissue anchor is disposed within the lumen. In some embodiments, the tissue anchor is disposed within the lumen such that a tissue piercing portion of the tissue anchor is disposed within the lumen. In some embodiments, the moving of the tissue anchor includes engaging the tissue anchor with a pusher that is movably disposed within the lumen.

In one embodiment, a medical device includes an elongate member defining a lumen and a tissue anchor. The elongate member has a retention member disposed within the lumen. The tissue anchor has a first arm portion, a second arm portion, and a base portion extending between the first arm portion and the second arm portion. The tissue anchor has a first configuration and a second configuration. The first arm portion is substantially linear when the tissue anchor is in its first configuration. The first arm portion is non-linear when the tissue anchor is in its second configuration. The tissue anchor is biased to its second configuration. The tissue anchor is configured to be disposed within the lumen defined by the elongate member such that the retention member engages the tissue anchor to help retain the tissue anchor in its first configuration.

In some embodiments, the first arm portion of the tissue anchor includes a tissue piercing portion. The tissue anchor is configured to be disposed within the lumen defined by the elongate member such that the tissue piercing portion is disposed within the lumen defined by the elongate member. In some embodiments, the tissue anchor is configured to be disposed within the lumen defined by the elongate member such that the entire tissue anchor is disposed within the lumen.

In some embodiments, the medical device includes a pusher disposed within the lumen defined by the elongate member. The pusher is configured to move from a first position within the lumen to a second position within the lumen. The first position within the lumen being different than the second position within the lumen.

In some embodiments, the medical device includes a pusher slidably disposed within the lumen defined by the elongate member. The pusher is configured to engage the tissue anchor and move the tissue anchor from a position within the lumen to a location outside of the lumen.

In some embodiments, the retention member includes a first portion configured to engage the first arm portion of the tissue anchor and a second portion configured to engage the second arm portion of the tissue anchor. In some embodiments, the retention member includes a first portion configured to engage the first arm portion of the tissue anchor and a second portion configured to engage the second arm portion of the tissue anchor. The second portion of the retention member is configured to help retain the second arm portion in a substantially linear configuration. In some embodiments, the retention member includes a flexible portion having a first configuration and a second configuration. The flexible portion is configured to be moved to from its first configuration to its second configuration to allow a movement of the tissue anchor within the lumen defined by the elongate member. In some embodiments, the retention member includes a flexible portion having a first configuration and a second configuration. The flexible portion is configured to be moved to from its first configuration to its second configuration to allow a movement of the tissue anchor within the lumen defined by the elongate member. The flexible portion of the retention member is biased to its first position.

In some embodiments, the tissue anchor is a first tissue anchor and the medical device includes a second tissue anchor having a first arm portion, a second arm portion, and a base portion extending between the first arm portion and the second arm portion. The second tissue anchor has a first configuration and a second configuration. The first arm portion is substantially linear when the tissue anchor is in its first configuration. The first arm portion is non-linear when the tissue anchor is in its second configuration. The second tissue anchor is biased to its second configuration. The second tissue anchor is configured to be disposed within the lumen defined by the elongate member while the first tissue anchor is disposed within the lumen such that the retention member engages the second tissue anchor to help retain the second tissue anchor in its first configuration.

In some embodiments, an apparatus includes an elongate member having a first end portion and a second end portion, a retention member, and a pusher. The elongate member defines a lumen configured to receive a tissue anchor such that a tissue piercing portion of the tissue anchor is disposed within the lumen. The retention member is disposed within the lumen defined by the elongate member. The retention member is configured to help retain at least a portion of the tissue anchor in a linear configuration. The pusher is configured to move within the lumen from a first position within the lumen to a second position within the lumen. The pusher is configured contact and force the tissue anchor from a location within the lumen to a location outside of the lumen in response to the pusher being moved from the first position to the second position.

In some embodiments, the tissue anchor is a first tissue anchor, the lumen defined by the elongate member is configured to receive a second tissue anchor such that a tissue piercing portion of the second tissue anchor is disposed within the lumen.

In some embodiments, the apparatus includes an actuator operatively coupled to the pusher and configured to move the positioner from its first position within the lumen to its second position within the lumen. In some embodiments, the pusher is biased to its first position.

In some embodiments, the apparatus includes a bias member disposed within the lumen and configured to engage the pusher and bias the pusher in its first position. In some embodiments, the apparatus includes a retainer configured to engage a portion of the pusher when the pusher is in its second position and help retain the pusher in its second position.

In some embodiments, a method of placing an anchor within a body of a patient, includes inserting a medical device within the body of the patient, the medical device includes an elongate member defining a lumen, and a tissue anchor disposed within the lumen, the tissue anchor having a first configuration in which an arm portion of the tissue anchor is substantially linear and a second configuration in which the arm portion is non-linear, the tissue anchor being biased to its first configuration; retaining the tissue anchor in its first configuration while the tissue anchor is disposed within the lumen defined by the elongate member; and moving the tissue anchor from a location within the lumen defined by the medical device to a location outside of the lumen.

In some embodiments, the retaining includes retaining the tissue anchor in its first configuration while the entire tissue anchor is disposed within the lumen defined by the elongate member. In some embodiments, the retaining includes retaining the tissue anchor in its first configuration while a tissue piercing portion of the tissue anchor is disposed within the lumen defined by the elongate member.

In some embodiments, the moving includes engaging the tissue anchor with a pusher of the medical device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   an elongate member defining a lumen, the elongate member having a retention member disposed within the lumen, the retention member including a first portion, a second portion, and a third portion, the third portion being disposed between the first portion and the second portion;
   a pusher configured to be at least partially disposed within the lumen defined by the elongate member, the pusher being configured to move from a first position within the lumen to a second position within the lumen in a first direction; and
   a tissue anchor having a first arm portion, a second arm portion, and a base portion extending between the first arm portion and the second arm portion, the tissue anchor having a first configuration and a second configuration, the first arm portion being substantially linear when the tissue anchor is in the first configuration, the first arm portion being non-linear when the tissue anchor is in the second configuration, the tissue anchor being biased to the second configuration,
   the tissue anchor being configured to be disposed within the lumen defined by the elongate member such that the first portion of the retention member engages the first arm portion of the tissue anchor and the second portion of the retention member engages the second arm portion of the tissue anchor to help retain the tissue anchor in the first configuration,
   the pusher is configured to push the tissue anchor out of the lumen by moving from the first position to the second position in the first direction, wherein when moving from the first position to the second position, the third portion of the retention member is configured to flex in the first direction from a first orientation to a second orientation to permit the tissue anchor to move beyond the retention member.

2. The medical device of claim 1, wherein the first arm portion of the tissue anchor includes a tissue piercing portion, the tissue anchor being configured to be disposed within the lumen defined by the elongate member such that the tissue piercing portion is disposed within the lumen defined by the elongate member.

3. The medical device of claim 1, wherein the tissue anchor is configured to be disposed within the lumen defined by the elongate member such that the entire tissue anchor is disposed within the lumen.

4. The medical device of claim 1, wherein the third portion of the retention member is biased to the first orientation.

5. The medical device of claim 1, wherein the pusher includes a proximal end portion, the proximal end portion of the pusher extending linearly from a proximal end of the elongate member.

6. The medical device of claim 1, wherein the first arm portion and the second arm portion cross when the tissue anchor is in the second configuration.

7. The medical device of claim 1, further comprising:
   a projection extending from a location outside of the lumen to a location inside the lumen, the projection configured to engage with the pusher to assist with preventing the pusher from moving distally beyond the second position,
   wherein the pusher defines a recess, and the projection is configured to engage the recess when the pusher is in the second position.

8. The medical device of claim 1, wherein the retention member includes a polymer material.

9. The medical device of claim 1, further comprising:
   a bias mechanism configured to bias the pusher to the first position within the lumen of the elongate member, the bias mechanism including a first contact portion coupled within the lumen of the elongate member, a second contact portion coupled to the pusher, and a biasing member disposed between the first contact portion and the second contact portion, wherein the biasing member includes a spring.

10. The medical device of claim 1, the tissue anchor being a first tissue anchor, the medical device further comprising:
    a second tissue anchor having a first arm portion, a second arm portion, and a base portion extending between the first arm portion of the second tissue anchor and the second arm portion of the second tissue anchor, the second tissue anchor having a first configuration and a second configuration, the first arm portion of the second tissue anchor being substantially linear when the second tissue anchor is in the first configuration, the first arm portion of the second tissue anchor being non-linear when the second tissue anchor is in the second configuration, the second tissue anchor being biased to the second configuration, the second tissue anchor being configured to be disposed within the lumen defined by the elongate member while the first tissue anchor is disposed within the lumen such that the retention member engages the second tissue anchor to help retain the second tissue anchor in its first configuration.

11. An apparatus comprising:

an elongate member having a first end portion and a second end portion, the elongate member defining a lumen configured to receive a tissue anchor such that a tissue piercing portion of the tissue anchor is disposed within the lumen;

a retention member disposed within the lumen defined by the elongate member, the retention member being configured to help retain at least a portion of the tissue anchor in a linear configuration, the retention member including a first portion, a second portion, and a third portion, the third portion being disposed between the first portion and the second portion; and a pusher configured to move within the lumen from a first position within the lumen to a second position within the lumen in a first direction, the pusher including a first portion disposed outside the lumen via a first opening defined by the first end portion of the elongate member, the first portion of the pusher extending proximally from the first end portion of the elongate member, the pusher including a second portion disposed inside the lumen, the pusher being configured contact and force the tissue anchor from a location within the lumen to a location outside of the lumen via a second opening defined by the second end portion of the elongate member in response to the pusher being moved from the first position to the second position, wherein, when the pusher is moved from the first position to the second position, the third portion of the retention member flexes in the first direction from a first orientation to a second orientation to permit the tissue anchor to move beyond the retention member.

12. The apparatus of claim 11, wherein the tissue anchor is a first tissue anchor, and the lumen defined by the elongate member is configured to receive a second tissue anchor such that a tissue piercing portion of the second tissue anchor is disposed within the lumen.

13. The apparatus of claim 11, further comprising:

an actuator operatively coupled to the pusher and configured to move the pusher from the first position within the lumen to the second position within the lumen.

14. The apparatus of claim 11, wherein the pusher is biased to the first position.

15. The apparatus of claim 11, further comprising a bias member disposed within the lumen and configured to engage the pusher and bias the pusher to the first position.

16. The apparatus of claim 11, further comprising:

a retainer configured to engage a portion of the pusher when the pusher is in the second position and help retain the pusher in the second position.

17. The apparatus of claim 11, further comprising:

a projection extending from a location outside of the lumen to a location inside the lumen, the projection configured to engage with a recess of the pusher to assist with preventing the pusher from moving distally beyond the second position.

* * * * *